(12) United States Patent
Schwendeman et al.

(10) Patent No.: US 6,326,021 B1
(45) Date of Patent: Dec. 4, 2001

(54) BIOCOMPATIBLE POLYMERIC DELIVERY SYSTEMS HAVING FUNCTIONAL GROUPS ATTACHED TO THE SURFACE THEREOF

(75) Inventors: Steven Schwendeman; Chengji Cui, both of Ann Arbor, MI (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/595,649

(22) Filed: Jun. 16, 2000

Related U.S. Application Data
(60) Provisional application No. 60/139,950, filed on Jun. 18, 1999.

(51) Int. Cl.$^7$ ............... A61F 2/00; A61K 9/14; A61K 9/50; A61K 9/70
(52) U.S. Cl. .......... 424/426; 424/484; 424/486; 424/489; 424/497; 424/443; 424/444
(58) Field of Search .................... 424/426, 428, 424/430, 434, 435, 436, 437, 443, 486, 489, 444, 497

(56) References Cited

U.S. PATENT DOCUMENTS
6,004,573 * 12/1999 Rathi et al. .......................... 424/426

OTHER PUBLICATIONS
"Nanoparticle Dna Carrier with Poly(L–lysine) Grafted Polysaccharide Copolymer and Poly(D,L–lactic acid)" by Maruyama, et al., *Bioconjugate Chem.* 1997, 8, 735–742.

"Resorbable polymeric microspheres for drug delivery—production and simultaneous surface modification using PEO–PPO surfactants" by Coombes, et al., *Biomaterials*, vol. 15, No. 9, 1994, pp. 673–680.

* cited by examiner

*Primary Examiner*—Thurman K. Page
*Assistant Examiner*—Blessing Fubara
(74) *Attorney, Agent, or Firm*—Calfee, Halter & Griswold LLP

(57) ABSTRACT

A method for making biocompatible polymeric matrices, particularly polymeric particles, that have functional groups on the surface thereof are provided. The method comprises: providing a biocompatible base polymer; providing a surface-active, functional polymer, hereinafter referred to as an "SAFP"; entangling chains of the base polymer with chains of the SAFP, both of which are in a mobile state; and then demobilizing the base polymer chains to form a polymeric particle or matrix having a specific geometry. Polymeric particles having functional groups on the surface thereof are also provided. The particles comprise a biocompatible base polymer and an SAFP. The SAFP comprises one or more interactive regions for physically cross-linking with the base polymer, and one or more hydrophilic regions. The particles have a core region and an outer region having a an outer surface. The core region contains a plurality of biocompatible base polymer chains. The outer region of the particle contains a plurality of biocompatible base polymer chains and the interactive regions of the SAFP. The hydrophilic functional region or regions of the SAFP chains extend from the surface of the particle when the particle is placed in an aqueous solution.

20 Claims, 5 Drawing Sheets

GRAFT (COMB) POLYMER

BLOCK POLYMER

BIOCOMPATIBLE POLYMERIC DELIVERY SYSTEMS HAVING FUNCTIONAL GROUPS ATTACHED TO THE SURFACE THEREOF

This application claims the benefit of U.S. Provisional Application No. 20 60/139,950, filed on Jun. 18, 1999.

BACKGROUND

In recent years a number delivery systems comprised of a biocompatible polymer and a drug for treating a particular disease or condition have been produced. Polymeric drug delivery systems include implantable devices, such as stents, that are implanted into particular regions of the body for localized delivery of the drug. Polymeric drug delivery systems also include specific geometrics such as for example, microspheres, nanospheres, and cylinders that are injected through a needle into the body of the patient, e.g. into a muscle or the blood stream. The particles are injected into the blood stream for systemic delivery or delivery to a specific site. Targeted delivery to a specific site maximizes drug action and minimizes side effects. The ability to minimize side effects is especially important in cancer chemotherapy, vaccine delivery, and diagnostic imaging.

In order to target polymeric particles to a particular tissue or region of the body, it is necessary to include functional groups, such as ligands and antibodies, on the surface of the polymeric particle. Functional groups are also included on the surface of polymeric particle to avoid clearance by the reticuloendothelial system (RES) Without such groups, sufficient quantities of the particles may not reach the targeted tissue or site. In certain cases, bioactive molecules, such as peptide vaccines and genes, may also be attached to the surface of polymeric particles.

Attempts have been made to attach functional groups or bioactive molecules to the polymeric particle by modifying the biocompatible polymers themselves. The most successful methods that are currently employed involve covalently linking conjugatable or ligatable groups to the biocompatible polymer (e.g. to form a block copolymer) prior to formation of the polymeric particle. Such methods result in the formation of a modified polymer or copolymer which, unfortunately, does not have the same physical bulk properties as the unmodified polymer. Such methods are also expensive, inefficient, and time consuming.

Accordingly, it is desirable to have new methods of making biocompatible polymeric delivery systems that have functional groups, including conjugatable groups, on the surface thereof.

SUMMARY OF THE INVENTION

The present invention provides new methods for making biocompatible polymeric matrices, particularly polymeric particles, that have functional groups on the surface thereof. The method comprises: providing a biocompatible base polymer, preferably a biodegradeable base polymer; providing a surface-active, functional polymer, hereinafter referred to as an "SAFP"; entangling chains of the base polymer with chains of the SAFP, both of which are in a mobile state; and then de-mobilizing the base polymer chains to form a polymeric particle or matrix having a specific geometry, e.g. sheet. Advantageously, the present method does not involve copolymerization of the SAFP chains with the base polymer. The present method modifies only the surface of the polymeric particle or sheet and, thus, retains the bulk properties of the base polymer. The present method provides a polymeric delivery system which can be used to slowly release drugs. The present method is simple and efficient.

The present invention also provides a polymeric particle having functional groups on the surface thereof. The particles comprise a biocompatible base polymer and an SAFP. The SAFP comprised at least one interactive region for physically cross-linking with the base polymer, preferably a plurality of interactive regions, and at least one hydrophilic region, preferably a plurality of hydrophilic regions. The particles have a core region and an outer region having a an outer surface. The core region contains a plurality of the biocompatible base polymer chains, which preferably are formed from a biodegradeable and bioresorbable base polymer. The outer region of the particle contains a plurality of biocompatible base polymer chains and the interactive regions of the SAFP. Preferably, the interactive region or regions of the SAFP chains penetrate into the outer region of the particle and thus, become entangled or physically cross-linked with one chain or, preferably, multiple chains of the base polymer. The hydrophilic functional region or regions of the SAFP chains extend from the surface of the particle when the particle is placed in an aqueous solution.

DETAILED DESCRIPTION OF THE INVENTION

The present invention provides a method for making a polymeric matrix having functional groups on the surface thereof. The method comprises providing a base polymer; providing an SAFP; physically cross-linking chains of the SAFP with chains of the base polymer, and then de-mobilizing the base polymer chains to form a solid polymeric particle or porous or nonporous sheet of any moldable shape.

The base polymer is a biocompatible polymer. As used herein the term biocompatible refers to a polymer that is approved for use in the body by the Food and Drug Administration. Examples of biocompatible polymers are poly (ethylene-covinyl acetate), and silicone rubber cross linked to poly (dimethyl siloxan sulfoxide) and derivatives thereof. Preferably, the base polymer is biodegradeable and bioresorbable. As used herein the term biodegradeable refers to a base polymer that breaks down into oligomeric and/or monomeric units over a period of time, typically hours to months, when implanted or injected into the body of a mammal. As used herein, a bioresorbable polymer is one whose degradative products are metabolized in vivo or excreted from the body via natural pathways. Such polymers include, for example, a polymer from the linear polyester family, such as polylactic acid, polyglycolic acid or polycaprolactone and their associated copolymers, e.g. poly (lactide-co-glycolide) at all lactide to glycolide ratios, and both L-lactide or D,L lactide. Polymers such as polyorthoester, polyanhydride, polydioxanone and polyhydroxybutyrate may also be employed. Preferably, the base polymer is amorphous, i.e., it is not crystalline. It is also preferred that the base polymer not generate crystalline residues upon degradation in vivo. Preferably, the weight-averaged molecular weight of the base polymer is above 10,000 daltons. The polydispersity, I=Mw/Mn, is preferably less than 2.5.

The surface active, functional polymer (SAFP) is composed of a polymeric-backbone having an interactive region for physically cross-linking with the base polymer. Preferably, the backbone of the SAFP comprises a plurality of interactive regions. The interactive regions of the SAFP penetrate into the dispersed phase of an oil in water emulsion. The SAFP also comprises a hydrophilic region carrying one or more functional groups. Preferably the SAFP comprises a plurality of hydrophilic regions for extending from the surface of the base polymer when the final particle is placed into an aqueous solution. The hydrophilic regions are components of the backbone or are pendant groups which are attached to the backbone. The SAFP is a homopolymer or, preferably, a random co-polymer or a triblock co-polymer. Preferably, the weight-averaged molecular weight of the SAFP is from 4000 to 25,000 daltons. Preferably the functional groups are from 1–50% by weight of the SAFP. The SAFP is soluble at the interphase.

The SAFP further comprises functional groups which are covalently bonded to the backbone of the SAFP or pendant groups which are attached to the hydrophilic region of the SAFP backbone. The functional groups encompass conjugatable groups such as for example amines, hydroxyls, carbonyls, thiols, and carboxylic acids for covalently bonding of other bioactive molecules to the surface of the particle. The linkages formed following conjugation of the bioactive molecules to the conjugatable groups include amides, esters, and thioethers. Examples of SAFP which have conjugatable functional groups include (poly) lysine, acetylated poly (lysine); poly (glutamic acid, and poly (oxyethylene)-poly (oxyproplene) copolymers. The functional groups also encompass bioactive molecules such as for example, ligands, antibodies, peptides, nucleic acids and compounds that allow the particles to avoid the RES. The ligands are employed to target the particles to cells having receptors which interact with the ligand. One example of a ligand which may be attached to the backbone of the SAFP is the folate ligand which is used to target molecules to cancer cells. The antibodies target the particles to cells which overexpress antigens that are immunospecific for the antibodies. Examples of nucleic acids that are suitable functional groups are cDNA and RNA molecules that encode a gene product and antisense DNA. Examples of peptides are synthetic peptide vaccines. One example of a bioactive molecule that allows the particles to avoid the RES is polyethylene glycol (PEG).

The base polymer chains are interacted with the SAFP chains under conditions that mobilize both the base polymer and the SAFP chains and that allow the SAFP chains to become physically entangled with the base polymer chains. Thereafter the base polymer chains are de-mobilized to provide a polymeric particle or matrix of specific geometry, e.g., a sheet.

Preferably, an oil in water/emulsion and evaporation method is used to form particles. Alternatively, an oil in oil emulsion may be used. In the oil in water emulsion method the base polymer is mobilized by dissolving in a organic solvent, such as for example methylene chloride, to provide a solution of the base polymer. An aqueous solution containing the SAFP is added to a solution of the base polymer and the resulting mixture vigorously agitated for a time sufficient to form an oil in water emulsion. Preferably, the amount of SAFP added to the mixture is less than 0.5% (w/w) compared to the base polymer so the bulk properties of the polymer in the final polymeric particle will be minimally effected. More preferably, the amount of SAFP added is less than 0.05% (w/w) compared to the base polymer. The temperature of the reaction is from 5–40° C. When an acetylated poly (lysine) is used as the SAFP, the preferred pH is about 8.0. When a non-acetylated poly (lysine) is used as the SAFP, the preferred pH is from about 10 to about 12.

The base polymer is then de-mobilized by evaporating the organic solvent. The resulting particles are microspheres or nanospheres, both of which are spherical receptacles comprising a polymeric matrix. Preferably, the microspheres have a diameter in the range of $200 \times 10^{-6}$ m to $0.5 \times 10^{-6}$ m range, more preferably 1–100 $\mu$m. Preferably the nanospheres have a diameter in the range of $20 \times 10^{-9}$ m to $1000 \times 10^{-9}$ m, more preferably 50 to 200 nm.

Optionally, a drug is added to the polymer solution for encapsulation or incorporation into the particle. Suitable drugs which may be incorporated into the particle are a cytotoxic drug, such as for example doxorubicin; an anticoagulant agent, such as heparin; an anti-oxidant such as vitamin E; compounds that regulate cellular proliferation, and anti-inflammatory drugs, such as corticosteroids. During formation of the particle, the drugs are incorporated into the bulk base polymer matrix.

The bioactive molecules, such as the ligands, the antibodies, and the peptides may be attached to the SAFP backbone prior to the time the SAFP is interacted with the base polymer. Alternatively, the bioactive molecules are attached to the particle via the conjugatable groups after formation of the particle.

Good results have been obtained using PLGA as the base polymer, an acetylated poly(L-lysine) as the SAPFP and an oil-in-water emulsion-solvent evaporation method.

Preferably, the SAFP is synthesized by exposing poly(L-lysine) to acetic anhydride.

Preferably, the molecular weight distribution of the poly (L-lysine) is 4,000 to 25,000. 30 Preferably, acetic anhydride is added in 300-fold to 700-fold excess compared to the lysine residues present (mol/mol) to obtain a partially acetylated poly(L-lysine) which has both hydrophilic and lipophilic characteristics. During microsphere formation, the lipophilic portion of the acetylated poly(L-lysine) is non-covalently connected to the microsphere through partial entanglement with the base polymer chains. The hydrophilic portion of each acetylated poly(L-lysine) molecule extends from the surface of the microsphere. The $\epsilon$-amino groups of the unacetylated lysines in the hydrophilic portion of the acetylated poly(L-lysine) are available for conjugation.

Good results have also been obtained using PLGA as the base polymer and poly-(L lysine) as the SAFP. PLGA (0.20 dl/g, 50/50) was dissolved in 750 mg of $CH_2Cl_2$ (1 ml). Poly-1-lysine was dissolved in 1.0 ml buffer (pH 10, 0.1 M Borax/NaOH) at a concentration of 0.5%. The polylysine solution was then added to the PLGA/$CH_2Cl_2$ solution and vortexed for 15–20 seconds. The resulting emulsion was then quickly poured into 100 ml hardening buffer (pH 10, 0.1M Borax/NaOH) and stirred for 2 hours. The mixture was then filtered through an 0.45 um membrane filter and washed three times with deionized and distilled water. The resulting microparticles are resuspended in a small amount of water and lypholized. The resulting microparticles have a diameter of 20–40 $\mu$m and contain 2–8 $\mu$mol of $\epsilon$-amino groups per gram of microsphere.

Polymeric sheets having functional groups on the surface thereof are made by swelling a sheet made of the base polymer using conventional techniques, such as heat or solvating in a solvent such as ethanol, and then contacting the swollen surface of the sheet with an aqueous solution containing the SAFP for preferably from 1 to 24 hours. Thereafter, the sheet is deswollen and, preferably, rinsed and dried to provide a polymeric sheet having functional groups on the surface thereof. The sheet can be formed into particles using standard methods.

Particles prepared as described above are useful for delivering or targeting drugs, diagnostic agents, vaccines and genes to the circulation or specific sites of a mammalian body.

EXAMPLES

The following examples are for purposes of illustration only and are not intended to limit the scope of the invention as defined in the claims which are appended hereto.

Example 1
Acetylated Poly(L-Lysine) (AP-1)

6 mL of room temperature aqueous poly(L-lysine) (MW 4,000–15,000) solution (1 mg/mL) was titrated to pH 10 with 0.2 N and 1.0 N NaOH. 22 $\mu$L (23.8 mg) of acetic anhydride (0.23 mmol) was added to the stirred poly(L-lysine) solution in 6 to 11 aliquots over a total of 15 to 30 minutes for an acetic anhydride to lysine residue ratio of five (mol/mol). After each addition, the pH was adjusted back to 10 with 5 N NaOH. The reaction was allowed to continue for 12 to 15 hours. The reaction mixture was dialyzed against distilled water and then lyophilized.

Example 2
Acetylated Poly(L-Lysine) 2 (AP-2)

6 mL of room temperature aqueous poly(L-lysine) (MW 4,000–15,000) solution (1 mg/nL) was titrated to pH 10 with 0.2 N and 1.0 N NaOH. 66 $\mu$L (71.3 mg) of acetic anhydride (2.35 mmol) was added to the stirred poly(L-lysine) solution in 6 to 11 aliquots over a total of 15 to 30 minutes for an acetic anhydride to lysine residue ratio of 15 (mol/mol). After each addition, the pH was adjusted back to 10 with 5 N NaOH. The reaction was allowed to continue for 12 to 15 hours. The reaction mixture was dialyzed against distilled water and then lyophilized.

Example 3
Acetylated Poly(L-Lysine) 3 (AP-3)

6 mL of room temperature aqueous poly(L-lysine) (MW 4,000–15,000) solution (1 mg/mL) was titrated to pH 10 with 0.2 N and 1.0 N NaOH. 133 $\mu$L (143.6 mg) of acetic anhydride (1.41 mmol) was added to the stirred poly(L-lysine) solution in 6 to 11 aliquots over a total of 15 to 30 minutes for an acetic anhydride to lysine residue ratio of 30 (mol/mol). After each addition, the pH was adjusted back to 10 with 5 N NaOH. The reaction was allowed to continue for 12 to 15 hours. The reaction mixture was dialyzed against distilled water and then lyophilized.

Example 4
Acetylated Poly(L-Lysine) 4 (AP-4)

6 mL of room temperature aqueous poly(L-lysine) (MW 4,000–15,000) solution (1 mg/mL) was titrated to pH 10 with 0.2 N and 1.0 N NaOH. 222 $\mu$L (240 mg) of acetic anhydride (2.35 mmol) was added to the stirred poly(L-lysine) solution in 6 to 11 aliquots over a total of 15 to 30 minutes for an acetic anhydride to lysine residue ratio of 50 (mol/mol). After each addition, the pH was adjusted back to 10 with 5 N NaOH. The reaction was allowed to continue for 12 to 15 hours. The reaction mixture was dialyzed against distilled water and then lyophilized.

Example 5
Acetylated Poly(L-Lysine) 5 (AP-5)

6 mL of room temperature aqueous poly(L-lysine) (MW 4,000–15,000) solution (1 mg/mL) was titrated to pH 10 with 0.2 N and 1.0 N NaOH. 444 $\mu$L (479.5 mg) of acetic anhydride (X mmol) was added to the stirred poly(L-lysine) solution in 6 to 11 aliquots over a total of 15 to 30 minutes for an acetic anhydride to lysine residue ratio of 100 (mol/mol). After each addition, the pH was adjusted back to 10 with 5 N NaOH. The reaction was allowed to continue for 12 to 15 hours. The reaction mixture was dialyzed against distilled water and then lyophilized.

Example 6
Acetylated Poly(L-Lysine) 6 (AP-6)

103 mL of room temperature aqueous poly(L-lysine) (MW 4,000–15,000) solution (5 mg/mL) was titrated to pH 10 with 0.2 N and 1.0 N NaOH. 3.325 mL (3.6 g) of acetic anhydride (35.3 mmol) was added to the stirred poly(L-lysine) solution in 6 to 11 aliquots over a total of 15 to 30 minutes for an acetic anhydride to lysine residue ratio of 300 (mol/mol). After each addition, the pH was adjusted back to 10 with 5 N NaOH. The reaction was allowed to continue for 12 to 15 hours. The reaction mixture was dialyzed against distilled water and then lyophilized.

Example 7
Acetylated Poly(L-Lysine) 7(AP-7)

3 mL of room temperature aqueous poly(L-lysine) (MW 4,000–15,000) solution (5 mg/mL) was titrated to pH 10 with 0.2 N and 1.0 N NaOH. 7.757 mL (0.4 g) of acetic anhydride (82.1 mmol) was added to the stirred poly(L-lysine) solution in 6 to 11 aliquots over a total of 15 to 30 minutes for an acetic anhydride to lysine residue ratio of 700 (mol/mol). After each addition, the pH was adjusted back to 10 with 5 N NaOH. The reaction was allowed to continue for 12 to 15 hours. The reaction mixture was dialyzed against distilled water and then lyophilized.

Example 8
PLGA Microspheres Comprising Acetylated Poly (L-lysine)

Poly(lactide-co-glycolide) ("PLGA") microspheres were prepared by oil-in-water emulsion-solvent evaporation methods. PLGA 50/50 (i.v. 0.20 dl/g, Birmingham Polymers, Inc.) was dissolved in methylene chloride at 750 mg/mL. 0.5 mL of polymer solution was emulsified with 0.5 mL of 0.1% (w/v) suspension of each of the poly(L-lysine)s described above in examples 1–6, in a buffer (0.005M, pH 8). Microspheres comprising PLGA and the acetylated poly (L-lysine)s were hardened in a bath containing 100 mL of buffer (0.05M, pH 8) for several hours. In some instances, in order to accelerate microsphere hardening, 1–5% isopropanol was used to help extract organic solvent from the microsphere. [The hardened microspheres were collected by centrifligation, washed and lyophilized.

Table I below contains the microencapsulation results of each synthesis.

TABLE I

Microencapsulation results for each acetylated-poly(L-lysine) synthesized.

| Surfactant | Acetic Anhydride/ Lysine Residues (mol/mol) | Microencapsulation Properties |
|---|---|---|
| AP-1 | 5 | "Large" Beads |
| AP-2 | 15 | (d ≈ 1 mm) |
| AP-3 | 30 | Particles Rapidly |
| AP-4 | 50 | Aggregated |
| AP-5 | 100 | Particles (30–120 μm) Aggregated in 10–60 min. |
| AP-6 | 300 | Stable Microspheres |
| AP-7 | 700 | (30–60 μm) |

Figure 1:
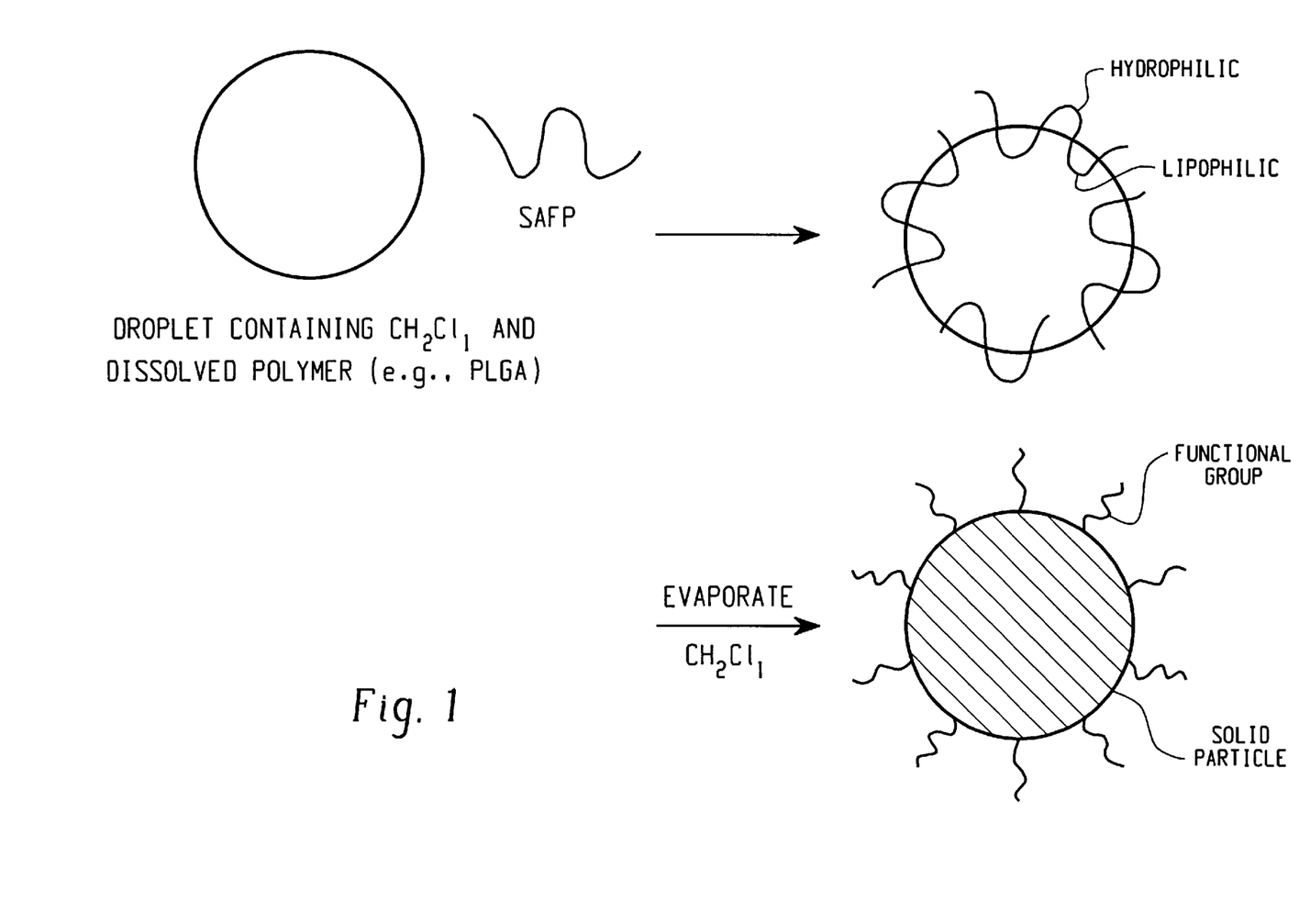
FIG. 1 is a schematic representation of a method used to prepare microspheres and nanospheres composed of a base polymer and an SAFP.
Figure 2:
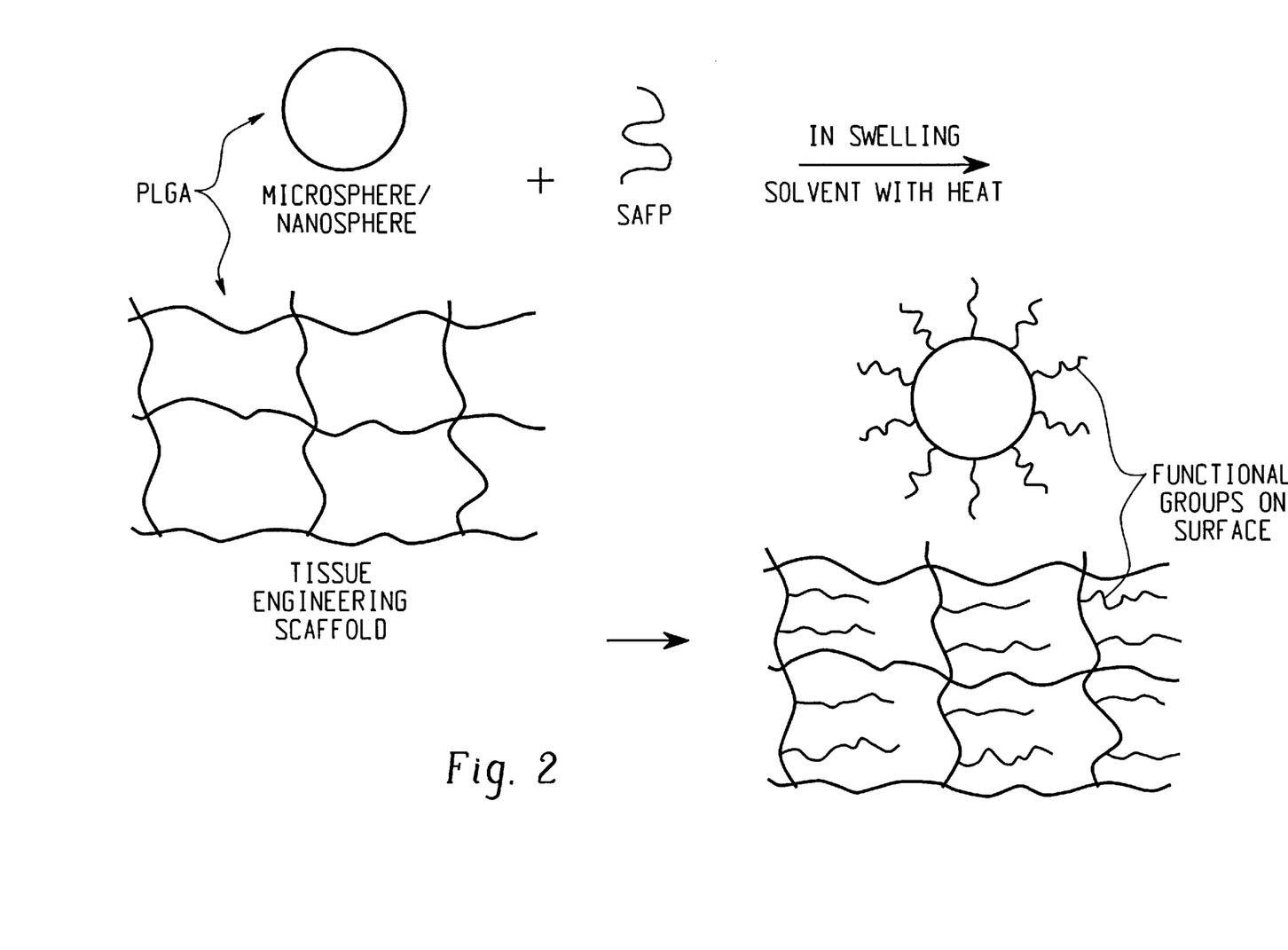
FIG. 2 is a schematic representation of a method used to incorporate an SAFP into the outer region of a pre-formed polymeric microsphere or nanosphere.
Figure 3A:
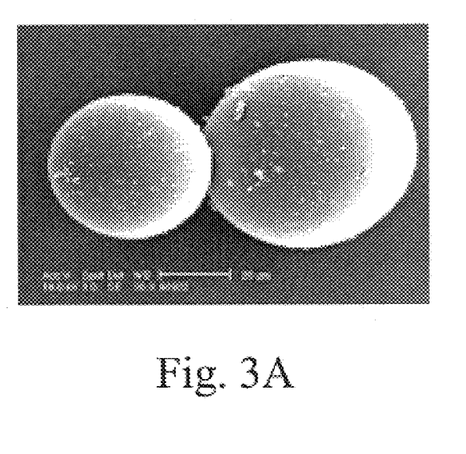
FIG. 3A is a scanning electron micrograph of poly (lactide-co-glycide) (PLGA) microspheres prepared from acetylated poly (L-lysine), AP-6.
Figure 3B:
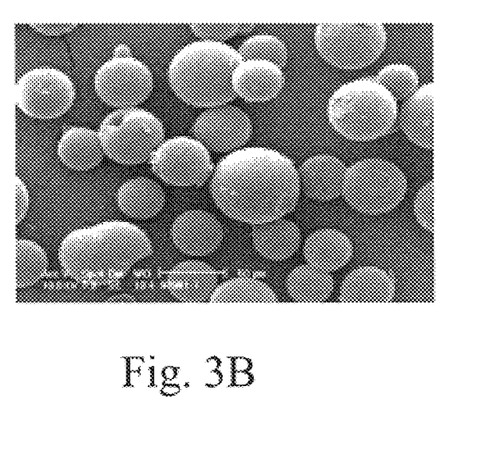
FIG. 3B is a scanning electron micrograph of poly (lactide-co-glycide) (PLGA) microspheres prepared from acetylated poly (L-lysine).

Acetylated poly(L-lysine) synthesized from varied molar ratio of acetic anhydride to lysine residues showed different microencapsulation properties. The higher the mole excess of acetic anhydride over lysine residues, the more stable the o/w emulsion, and the better microspheres that could be obtained. Microspheres prepared from AP6 and AP7 were spherical with a relatively smooth surface, indicated by scanning electron micrography (See FIG. 3), and their size was about 30–60 μm.

Determination of Free ε-amino Groups on the Surface of Microspheres Comprising AP-6 and AP-7.

Figure 4:
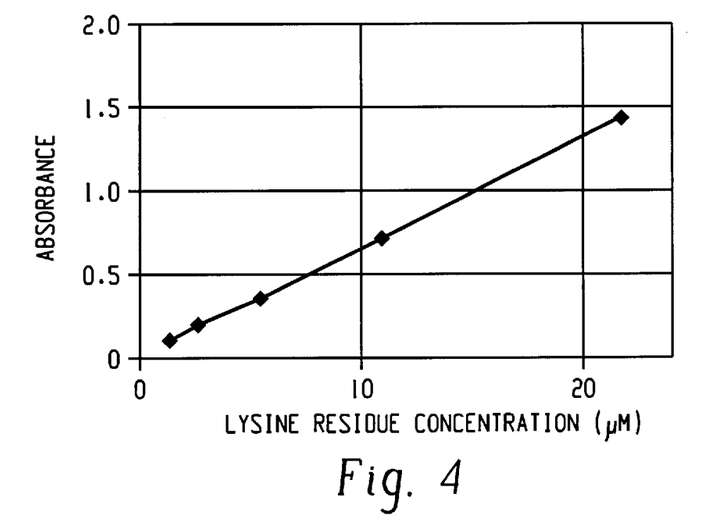
FIG. 4 depicts the calibration curve of lysine residue determination on the surface of PLGA microspheres prepared from acetylated poly (L-lysine).

Sulfo-succinimidyl-4-0-(4,4'-dimethoxytrityl)-butyrate (sulfo-SDTB) was obtained from Pierce. A fresh stock solution of the reagent was prepared as follows: sulfo-SDTB was dissolved in DMF and then mixed in a sodium bicarbonate buffer (50 mM, pH 8.5) at a 5–10% v/v ratio (DMF/buffer). The final sulfo-SDTB concentration was 1 mM. Five standards were prepared by serial dilutions with 35% perchloric acid, which were used to prepare a calibration curve for the 4,4'-dimethoxytrityl cation. Microspheres were incubated with 1 mM sulfo-SDTB stock solution for 2–10 minutes. Excess reagent was discarded and the microspheres were washed thoroughly. With the addition of 2 ml 35% percholoroic acid, microspheres were dissolved and then the solution was filtered through a 0.22 μm Millipore membrane. Absorbance readings of the 4,4'-dimethoxytrityl cation were taken at a wavelength of 498 nm using a Diode-array UV/Vis spectrophotometer zeroed with 35% perchloric acid solution. Results of lysine residue determination by sulfo-SDTB showed the presence of free amino groups on microsphere surface. A calibration curve of lysine residue determination is shown in FIG. 4. The content of free amino groups on the surface of microspheres prepared from AP6 and AP7 is about 2 μmole per gram of bulk polymer, which corresponds to a AP loading of 0.03% (w/w).

RESULT OF LYSINE RESIDUE DETERMINATION

| | Lysine residue on PLGA microspheres (umol/g) | Surfactant loading (%, w/w) | % of initial lysine residues incorporated |
|---|---|---|---|
| Microspheres (AP-6) | 2.3 | 0.03% | 33.7% |
| Microspheres (AP-7) | 2.2 | 0.03% | 28.6% |

Free ε-amino ligatable functional group concentration was determined to be about 2 μmol per gram of bulk polymer. This level of free ε-amino groups corresponds to a surfactant loading of 0.03% (w/w), which is much lower than the 2% loading level that would effect polymer bulk properties if the poly lysine was co-polymerized with the PLGA as a block copolymer.

Retention Kinetics of Polylysine on the Surface of Microspheres Comprising AP-6 and AP-7

Retention kinetics of the conjugatable free amino groups on the microspheres surface was studied in phosphate buffered saline (PBS) at 37° C. Retained content of unmodified lysine residues on microsphere surface was determined by sulfo-SDTB as described above.

Figure 5:
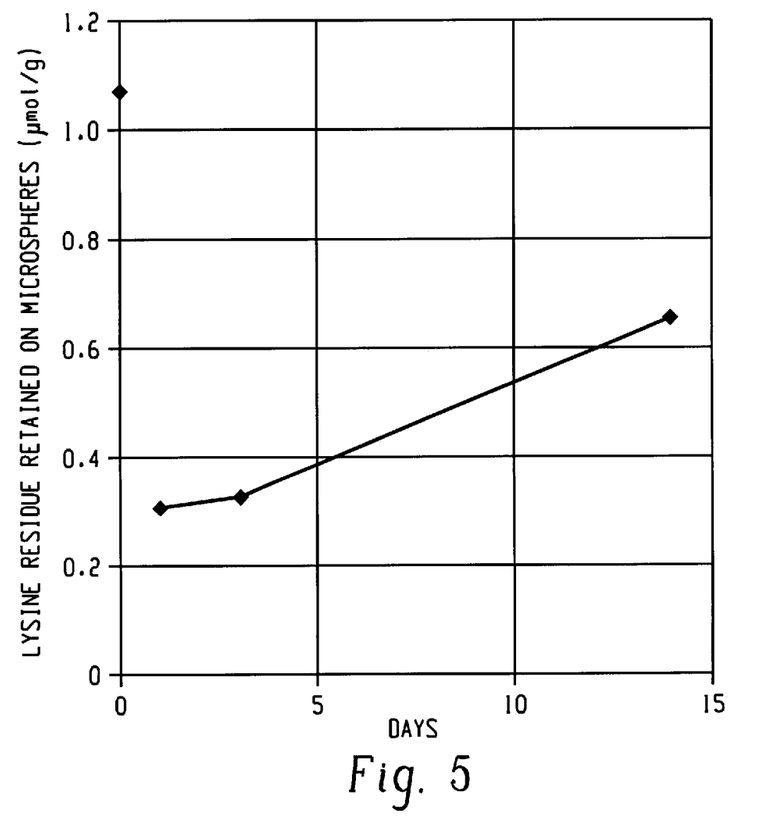
FIG. 5 shows the extent of retention of polylysine on PLGA microspheres prepared from acetylated poly (L-lysine).
Figure 6:
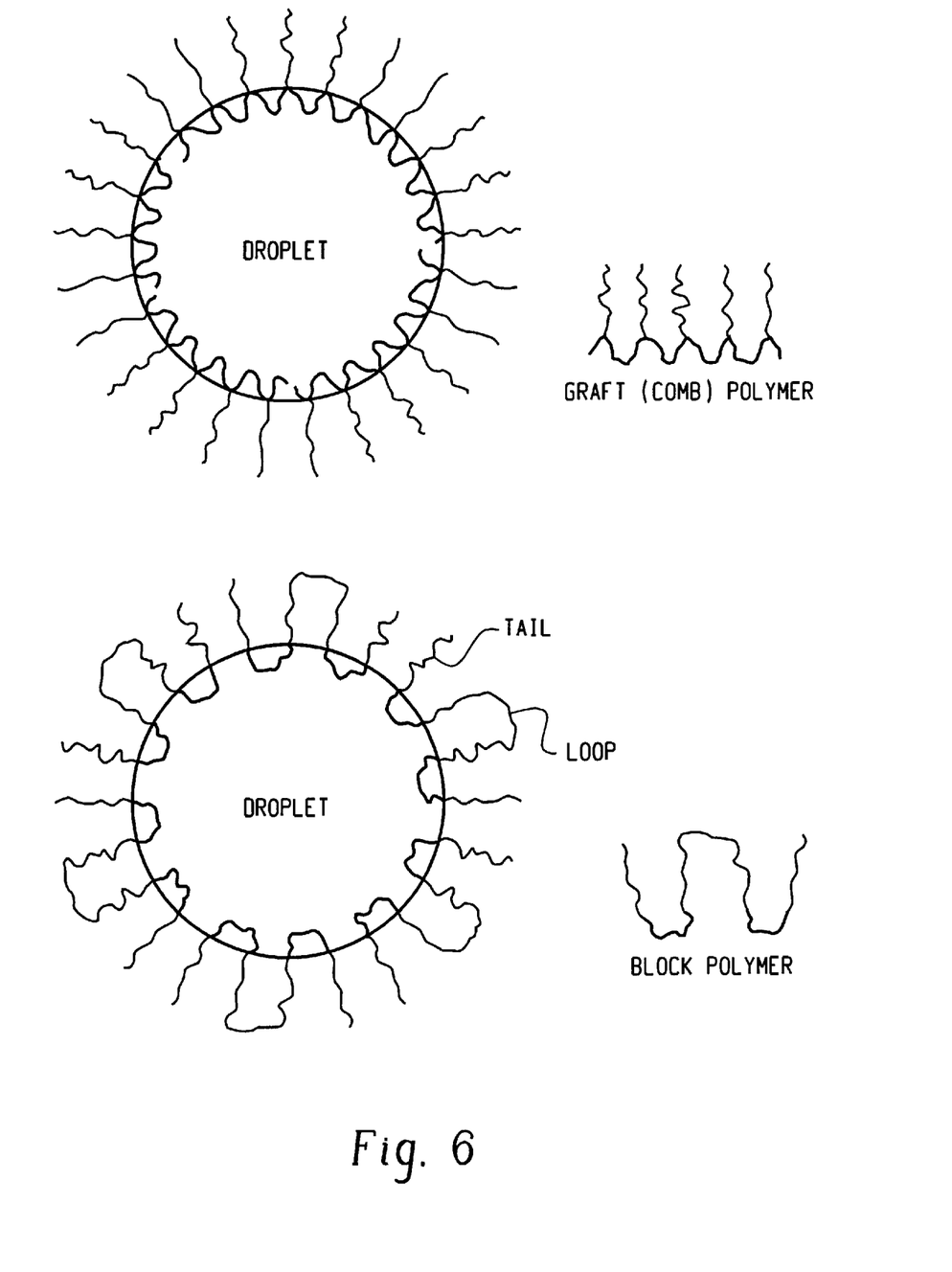
FIG. 6 is a schematic diagram of possible configurations of the SAFP at an emulsion droplet surface.

Retention of unacetylated lysine residues on microspheres surface is shown in FIG. 5. A significant portion of the lysine residues was retained on the microsphere surface for more than two weeks. Hydrolysis of AP and easier access of sulfo-SDTB to the buried free amino groups may have contributed to the increased lysine content on the microsphere surface between 3 days and two weeks. Thus, a significant portion of the lysine residues were retained on the microsphere surface for two weeks.

Example 9

PLGA Microspheres Having Albumin Conjugated to the ε-amino Groups of Acetylated Poly (L-lysine)

Bovine serum albumin (BSA) was conjugated to the ε-amino Groups of the acetylated poly (L-lysine) in the microspheres prepared as described above in example 7. Commercial BSA was partially reduced with dithiothreitol (DTT) before conjugation. SH groups on BSA molecules were detected by Ellman's assay. S-carboxymethyl-albumin was used as a control reagent to determine the non-specific adsorption of BSA to the microspheres. Conjugation or adsorption of BSA on the microspheres was determined by the decrease in the amount of BSA in the incubating solution. The results are shown in the Table below:

RESULT OF CONJUGATION OF ALBUMIN (BOVINE) REDUCED OR S-BLOCKED, TO THE MICROSPHERES

| Protein used in conjugation | Protein retained on microsphere |
|---|---|
| Reduced BSA (6.7 SH/BSA) | 46.4 mg BSA/g microsphere |
| S-carboxymethyl-BSA | 0 |

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

What is claimed is:

1. A method for preparing a biocompatible polymeric matrix having functional groups on the surface thereof, comprising:
   a) providing a first solution comprising a poly lactide-co-glycolide base polymer and an organic solvent;
   b) providing a second solution comprising a surface-active functional polymer and a solvent;
   c) mixing said first solution with said second solution to provide an emulsion in which chains of the base polymer become physically entangled with chains of the surface-active polymer; and
   d) evaporating said organic solvent to provide a polymeric matrix comprising chains of the base polymer which are physically entangled with chains of the surface-active polymer.

2. The method of claim 1 wherein said surface active polymer comprises
   a) a backbone having one or more interactive group for physically entangling with chains of said base polymer and one or more hydrophilic regions; and
   b) one or more functional groups which are covalently bonded to the backbone or are pendant groups which are attached to hydrophilic regions of the backbone.

3. The method of claim 2 wherein the functional groups are conjugatable groups for covalently bonding bioactive molecules to the surface of the polymeric matrix or bioactive molecules.

4. The method of claim 1 wherein the surface-active polymer is selected from the group consisting of poly (lysine), acetylated poly(lysine), and poly(glutamic acid.

5. The method of claim 1 wherein an oil-in-water or an oil-in-oil emulsion method is used to make said matrix.

6. The method of claim 1 wherein the amount of the surface active polymer in the mixture is less than 0.5% (w/w) of the base polymer.

7. A polymeric particle having an outer surface, said polymeric particle comprising:
   a) a poly lactide-co-glycolide base polymer; and
   b) a surface-active polymer, said surface active polymer comprising
      i) a backbone having one or more interactive regions which are physically entangled with said base polymer and one or more hydrophilic regions which extend from the surface of said particle when said particle is placed in an aqueous solution, and
      ii) one or more functional groups which are covalently bonded to the backbone of said surface-active polymer or are pendant groups which are attached to hydrophilic regions of the backbone of said surface-active polymer.

8. The polymeric particle of claim 7 wherein the functional groups are conjugatable groups for covalently bonding bioactive molecules to the surface of the polymeric matrix or bioactive molecules.

9. The polymeric particle of claim 7 wherein the surface-active polymer is selected from the group consisting of poly(lysine), acetylated poly(lysine), and poly(glutamic acid).

10. The polymeric particle of claim 8 wherein the bioactive molecule is selected from the group consisting of a ligand, an antibody, a peptide, a nucleic acid and a compound which allows the particle to avoid the reticuloendothelial system.

11. The polymeric particle of claim 7 wherein the loading level of the surface-active polymer is less than 2% (w/w) of the base polymer.

12. The polymeric particle of claim 11 wherein the loading level of the surface-active polymer is less than 1% (w/w) of the base polymer.

13. The polymeric particle of claim 7 wherein said particle further comprises a drug incorporated therein.

14. The polymeric particle of claim 8 wherein the conjugatable groups are selected from the group consisting of amines, hydroxyls, carbonyls, thiols, and carboxylic acids.

15. The polymeric particle of claim 8 wherein the bioactive molecules are conjugated to the surface active polymer by an amide, ester, or thioether linkage.

16. A polymeric particle having an outer surface, said polymeric particle comprising:
   a) a poly lactide-co-glycolide base polymer; and
   b) a surface-active polymer, said surface active polymer comprising
      i) a backbone having one or more interactive regions which are physically entangled with chains of said base polymer and one or more hydrophilic regions which extend from the surface of said particle when said particle is placed in an aqueous solution, and
      ii) one or more functional groups which are covalently bonded to the backbone or are pendant groups which are attached to hydrophilic regions of the backbone wherein the surface active polymer is a poly (L-lysine) or acetylated poly (L-lysine).

17. A method for preparing a biocompatible polymeric matrix having functional groups on the surface thereof, comprising:
   a) swelling a polymeric sheet comprising a bicompatible and bioresorbable base polymer,
   b) contacting said sheet with a solution comprising a surface-active functional polymer and a solvent for a time sufficient to allow chains of the base polymer to become entangled with chains of the surface-active polymer, and
   c) deswelling the polymeric sheet.

18. The method of claim 17 wherein the base polymer is poly lactide-co-glycolide.

19. The method of claim 17 wherein the polymeric sheet is swollen by heating or by solvating in a solvent.

20. The method of claim 17 wherein the surface active polymer is is selected from the group consisting of poly (lysine), acetylated poly(lysine), and poly(glutamic acid).

* * * * *